(12) United States Patent
Haun

(10) Patent No.: US 9,301,859 B2
(45) Date of Patent: Apr. 5, 2016

(54) FORESHORTENED PROSTHETICS FOR BILATERAL LEG AMPUTEES

(75) Inventor: Dennis G. Haun, Fallston, MD (US)

(73) Assignee: H. Lee Mantelmacher, Owings Mils, MD (US)

( * ) Notice: Subject to any disclaimer, the term of this patent is extended or adjusted under 35 U.S.C. 154(b) by 1250 days.

(21) Appl. No.: 12/657,666

(22) Filed: Jan. 25, 2010

(65) Prior Publication Data

US 2010/0198360 A1  Aug. 5, 2010

Related U.S. Application Data

(60) Provisional application No. 61/205,965, filed on Jan. 26, 2009.

(51) Int. Cl.
- *A61F 2/66* (2006.01)
- *A61F 2/80* (2006.01)
- *A61F 2/50* (2006.01)

(52) U.S. Cl.
CPC ............. *A61F 2/66* (2013.01); *A61F 2/6607* (2013.01); *A61F 2/80* (2013.01); *A61F 2002/5003* (2013.01); *A61F 2002/5079* (2013.01); *A61F 2002/6657* (2013.01)

(58) Field of Classification Search
USPC .......................... 623/27–28, 53–56
See application file for complete search history.

(56) References Cited

U.S. PATENT DOCUMENTS 5,376,141 A * 12/1994 Phillips ........................... 623/55
2005/0033451 A1 * 2/2005 Aigner et al. ................... 623/53

* cited by examiner

*Primary Examiner* — Bruce E Snow
(74) *Attorney, Agent, or Firm* — Ober, Kaler, Grimes & Shriver; Royal W. Craig

(57) ABSTRACT

A foreshortened prosthesis comprising a socket, an adapter attached distally to said socket, and a foot attached to the adapter. The foot comprises a lower base plate formed as a flat peripherally-curvilinear member fixedly attached to the adapter and defining a short toe, a longer heel, and an instep there between. In addition, an upper slide plate is sandwiched between the adapter and lower base plate, but is not otherwise attached to the lower base. The upper slide plate is smaller and narrower than the lower base plate and slides there against under the weight of a heel strike, thereby serving as a leaf spring damper and suspension to smooth ambulation. This provides a BAK amputee with a more comfortable and natural gait, at a suitable angle and orientation, with smooth and comfortable flex relative to the direction of travel.

18 Claims, 4 Drawing Sheets

Fig. 1 9 (Prior Art)

FORESHORTENED PROSTHETICS FOR BILATERAL LEG AMPUTEES

CROSS-REFERENCE TO RELATED APPLICATION(S)

The present application derives priority from U.S. Provisional application Ser. No. 61/205,965 filed 26 Jan. 2009.

BACKGROUND OF THE INVENTION

1. Field of the Invention

The present invention relates to prosthetics and, more particularly, to foreshortened prosthetic legs ("Stubbies") for bi-lateral above-the-knee amputation patients.

2. Description of the Background

There are a variety of different types of prosthetic devices for patients that have had either transfemoral (above-knee) or transtibial (below the knee) amputation. A typical modern prosthetic device consists of a custom socket fitted over the residual limb, a structural component system affixed to the socket that may include a pylon and articulated replacement joints (such as a knee or ankle) depending on the patient and location of the amputation, and knee cuffs, belts or other systems to secure the device to the body. A prosthetic sock or liner is typically worn over the residual limb within the socket to cushion the area of contact, and, in some cases, realistic-looking skin is provided over the structural components for aesthetic reasons.

One of the primary concerns of all prosthetic designs and construction is that the device be lightweight and provide a comfortable fit to the residual limb, and a natural gait when in use. This is an especially acute problem for bilateral above-knee amputees (BAKs). Because of the total loss of knee function most BAKs find prosthetic walking to be stressful and impracticable, especially the elderly. Indeed, very few BAKs can keep ambulatory control at all when using conventional bilateral leg prostheses. "Stubbies" are short prostheses comprising a standard socket, a leg with no articulated knee joints, and attached feet. Although stubbies are generally used as post-operative training devices to determine an amputee's ability to move to a standard, full-length prosthesis, they are also used for showering and other activities by amputees across the world.

Stubbies can include a variety of foot designs, ranging from standard prosthetic ankle/feet to rocker bottom platforms. If standard prosthetic feet are to be utilized, they are often set in a backwards position, with the heels facing the front. This is to help prevent the amputee from falling backwards. Rocker bottoms, although not realistic looking, offer greater anterior and posterior horizontal support. This increased ground level support provides an increased level of stability for the user. The typical rocker bottom foot design allows the bilateral leg amputee to achieve a lower center of gravity for better balance and stability. FIG. 1 is a perspective view of a pair of stubbies having prior art circular-platform feet.

Stubbies with rocker bottom feet are relatively easy to use, but are not conducive to ambulation because the platform feet typically cannot bend.

To provide the BAK amputee with a more comfortable and natural gait, it is of primary concern that a prosthetic foot be disposed at a suitable angle and orientation, be shaped appropriately, and flex properly relative to the direction of travel. These design criteria are not met by conventional stubby prostheses using rocker-bottom feet, and so it would be greatly advantageous to develop a stubby prosthetic with improved rocker bottom foot for improved ambulation.

SUMMARY OF THE INVENTION

Accordingly, it is an object of the present invention to provide a foreshortened (stubby) prosthetic with improved resilient foot having a predetermined flexure profile for improved ambulation of bi-lateral above-the-knee amputation patients.

The above and other objects, features and advantages of the present invention will become readily apparent from the following detailed description thereof which is to be read in connection with the accompanying drawings, in which a foreshortened prosthesis is described. The prosthesis generally comprises a socket, an adapter attached distally to said socket, and a foot attached to the adapter. The foot further comprises a lower base plate formed as a flat peripherally-curvilinear member fixedly attached to the adapter and defining a short toe, a longer heel, and an instep there between. In addition, an upper slide plate is sandwiched between the adapter and lower base plate, but is not otherwise attached to the lower base. The upper slide plate is smaller and narrower than the lower base plate and slides there against under the weight of a heel strike, thereby serving as a leaf spring damper and suspension to smooth ambulation. This provides a BAK amputee with a more comfortable and natural gait, at a suitable angle and orientation, with smooth and comfortable flex relative to the direction of travel.

BRIEF DESCRIPTION OF THE DRAWINGS

Other objects, features, and advantages of the present invention will become more apparent from the following detailed description of the preferred embodiment and certain modifications thereof, in which.

DETAILED DESCRIPTION OF THE PREFERRED EMBODIMENTS

The present invention is a foreshortened (stubby) prosthesis with improved rocker-bottom feet to provide BAK amputees with stability plus a more comfortable and natural gait. The rocker-bottom foot is disposed at a suitable angle and orientation, is contoured appropriately for a smooth gait, and flexes uniformly along the direction of travel, all for improved ambulation.

Figure 1:
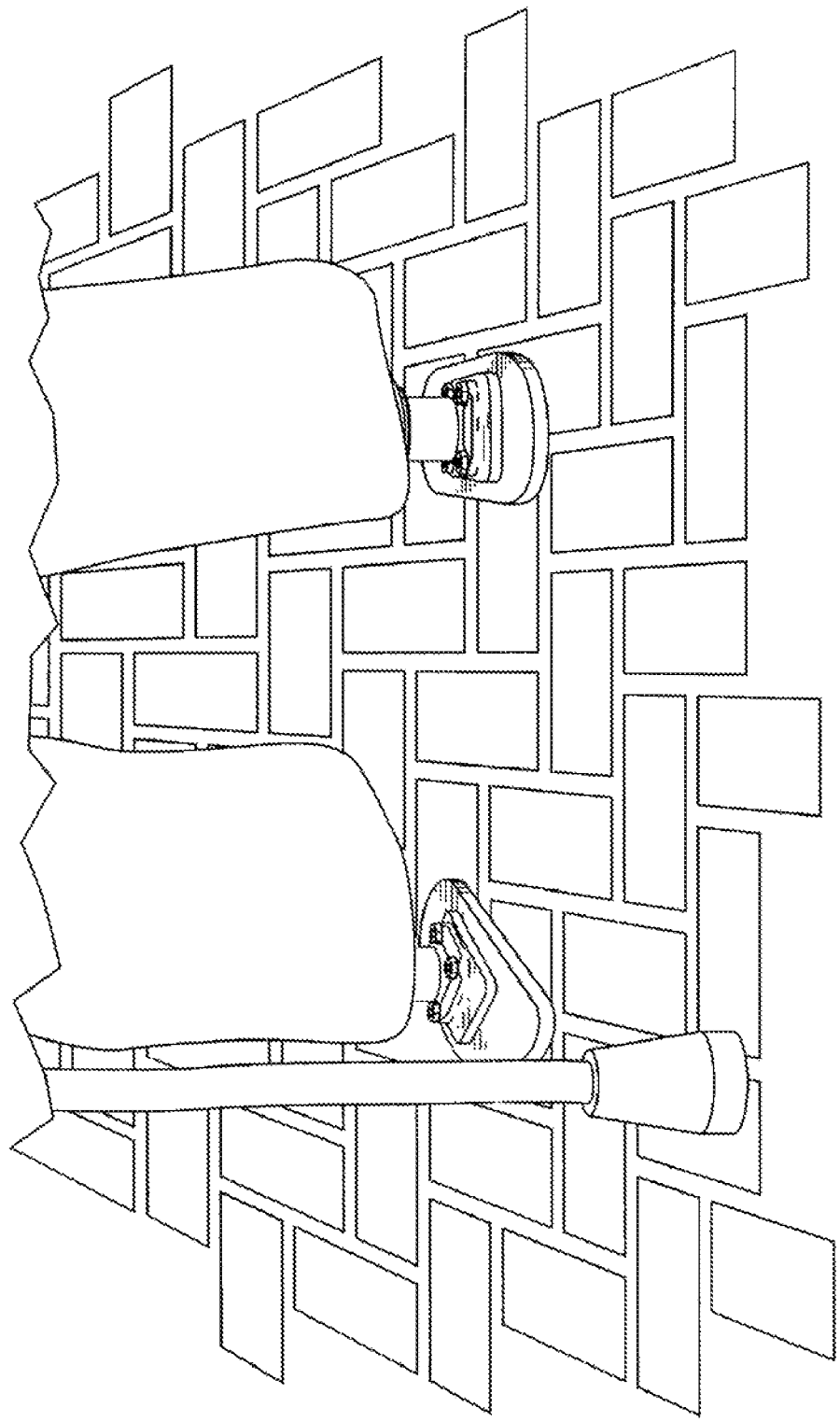
FIG. 1 is a perspective view of a pair of foreshortened prosthetic legs "Stubbies") having prior art circular-platform rocker feet.
Figure 2:
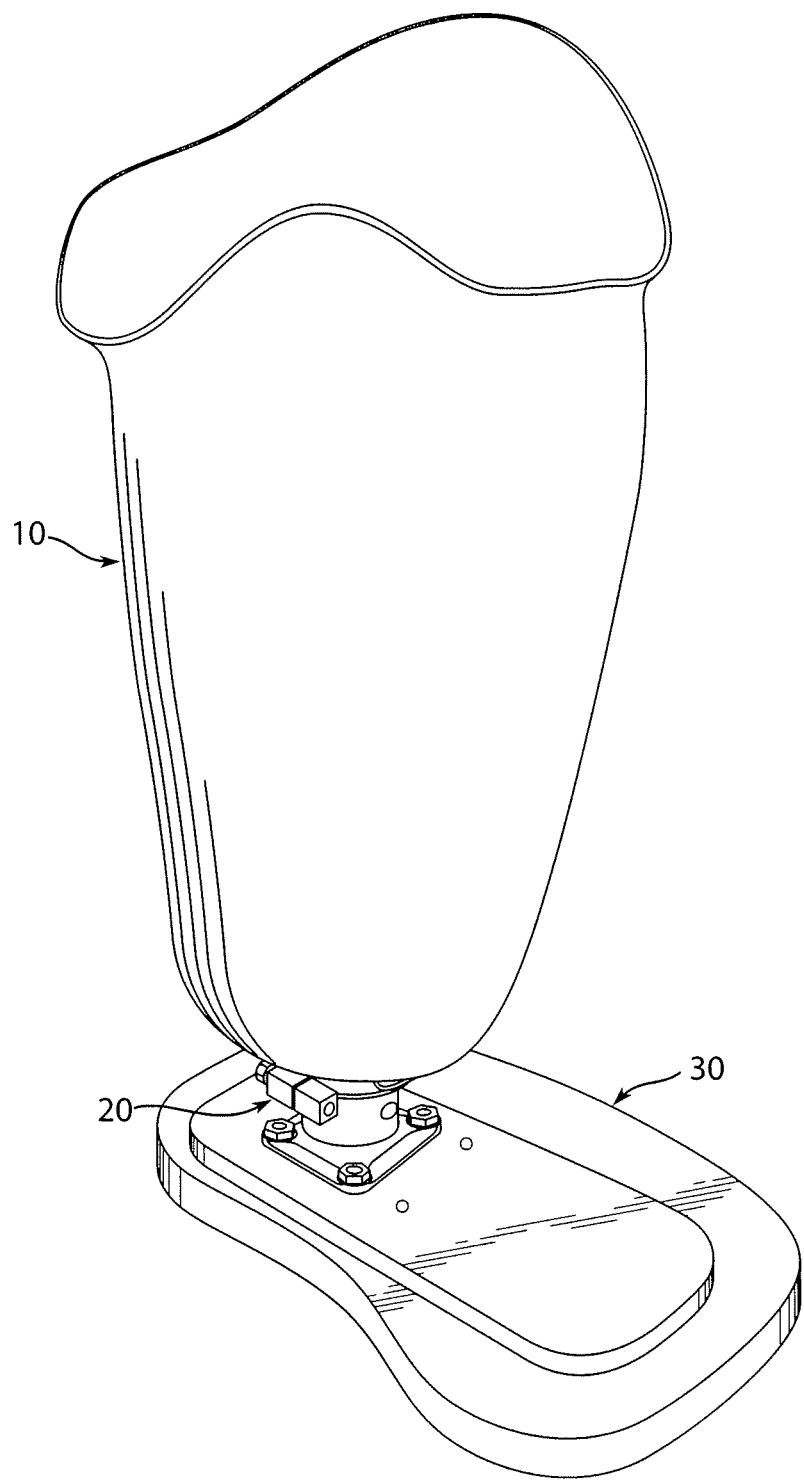
FIG. 2 is a rear perspective view of the prosthetic according to the present invention.

FIG. 2 is a perspective view of a foreshortened prosthesis (viewed from the rear) according to the present invention, which generally includes a socket 10, adapter 20, and foot 30.

Socket 10 is generally a conventional socket formed of plastic, typically vacuum formed. The socket 10 is a custom-fitted component that is made in a conventional manner of a copolymer plastic, plastic polypropylene, polyester, acrylic/epoxy resin, or the like, the illustrated socket being reinforced with woven fabric. The socket 10 may be vacuum formed or thermoformed by heating the plastic material and forming it over a mold as is known in the art.

The distal end of the socket 10 is connected to a conventional, non-articulating adapter 20 (a variety of which are presently commercially available). The adapter 20 serves the function of connecting the socket 10 to the foot 30 and maintaining proper alignment there between. For example, the adapter 20 may comprise a standard aluminum 3- or 4-prong socket adapter fixedly connected to a 4-hole male pyramid base, which is in turn attached to the foot 30. Both of these exemplary components are readily available from, for example, Ossur Americas at 27412 Aliso Viejo Pkwy, Aliso Viejo, Calif. 92656.

The foot 30 comprises a bi-planar structure including a resilient upper slide plate 32 and a resilient lower base plate 34. The upper slide plate 32 is a substantially rectangular structure here approximately 7" long by 3" wide and ½" thick, though dimensions may vary. The upper slide plate 32 may be molded or cut from a sheet of plastic, preferably a homopolymer such as Delrin™ or a copolymer such as acetal copolymer, or like plastic exhibiting a combination of high strength, a balanced resilience/stiffness, ease of machining, and low coefficient of friction properties. The lower base 34 is a flat peripherally-curvilinear structure here approximately 10" long by 5" wide and ¾" thick, though again dimensions may vary. It is important that both the width and length dimensions of the lower base 34 be at least 5% greater than those of the slide plate 32, and more preferably 15-30% greater. The lower base plate 34 may be molded or cut from a sheet of plastic, preferably a copolymer such as acetal copolymer, or the like. The added thickness of the lower base plate 34 increases its relative strength and stiffness, but reduces the resilience, while maintaining the same low coefficient of friction properties. Preferably, a softened rubber pad 37 is adhered to the bottomside of the lower base for impact absorption and wear resistance, and a variety of known shoe sole materials suffice for this purpose such as Vibram™. A 1-3 mm pad 37 conforming to the lower base plate 34 will suffice.

Figure 3:
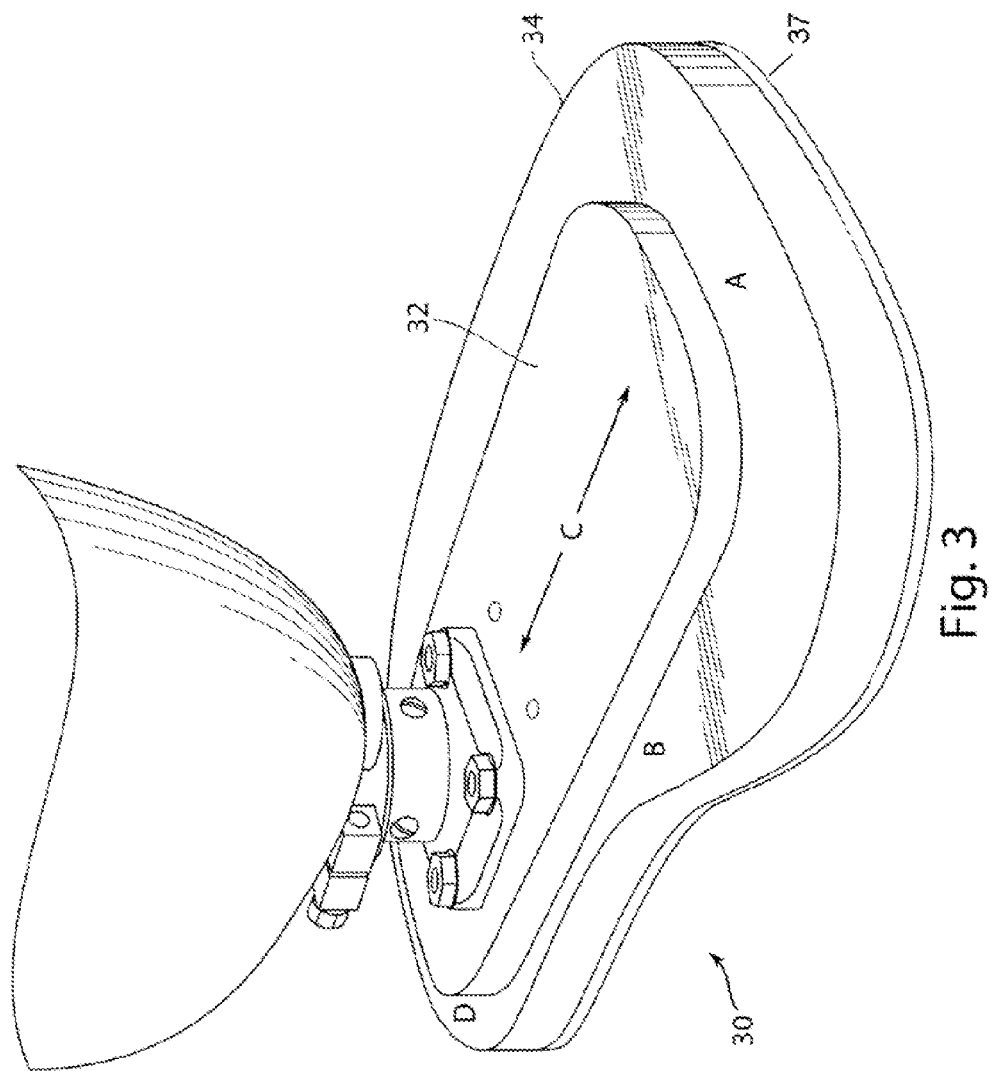
FIG. 3 is an enlarged rear perspective view of the prosthetic as in FIG. 2.

FIG. 3 is an enlarged rear perspective view of the prosthetic as in FIG. 2, again a rear view. The lower base plate 34 is loosely shaped as a reversed duck foot, which increases ambulatory stability during ambulation and reduces exertion. More specifically, the different areas of the lower base plate 34 defined in podiatric terms include the heel (A), instep (B), metatarsus (C), and toe (D). The toe (D) extends forwardly of the adapter 20 and generally defines a half-circle circumscribing the adapter 20. The toe (D) segways into the elongate metatarsus portion (C) which extends rearwardly to a broadened heel (A). The heel (A) is truncated along a broader U-shaped arch, while the toe (D) is truncated along a smaller circular arch, the instep (B) occurring between the heel (A) and toe (D) on the inside of the foot 30. The instep (B) defines an approximate ½-1" indented contour along the side of the foot 30. The outer side of the foot 30 is defined by a shallow outward arch.

The upper slide plate 32 is formed as a generally rectangular member with rounded corners, slightly smaller than the lower base plate 34 and fitting completely within the peripheral edges of the lower base plate 34 leaving a varying ¼" to 1.5" margin there around.

The adapter 20 is screwed down through the upper slide plate 32 and fixedly into the lower base plate 34, thereby sandwiching the upper slide plate 32. The upper slide plate 32 is not otherwise attached to the lower base plate 34 and given relative flexure between these components their abutting surfaces are intended to slide.

In use during ambulation, as the user strides forward the footplant begins at the heel (A) and as weight is placed upon the heel (A) the lower base plate 34 bends as weight is applied.

Figure 4:
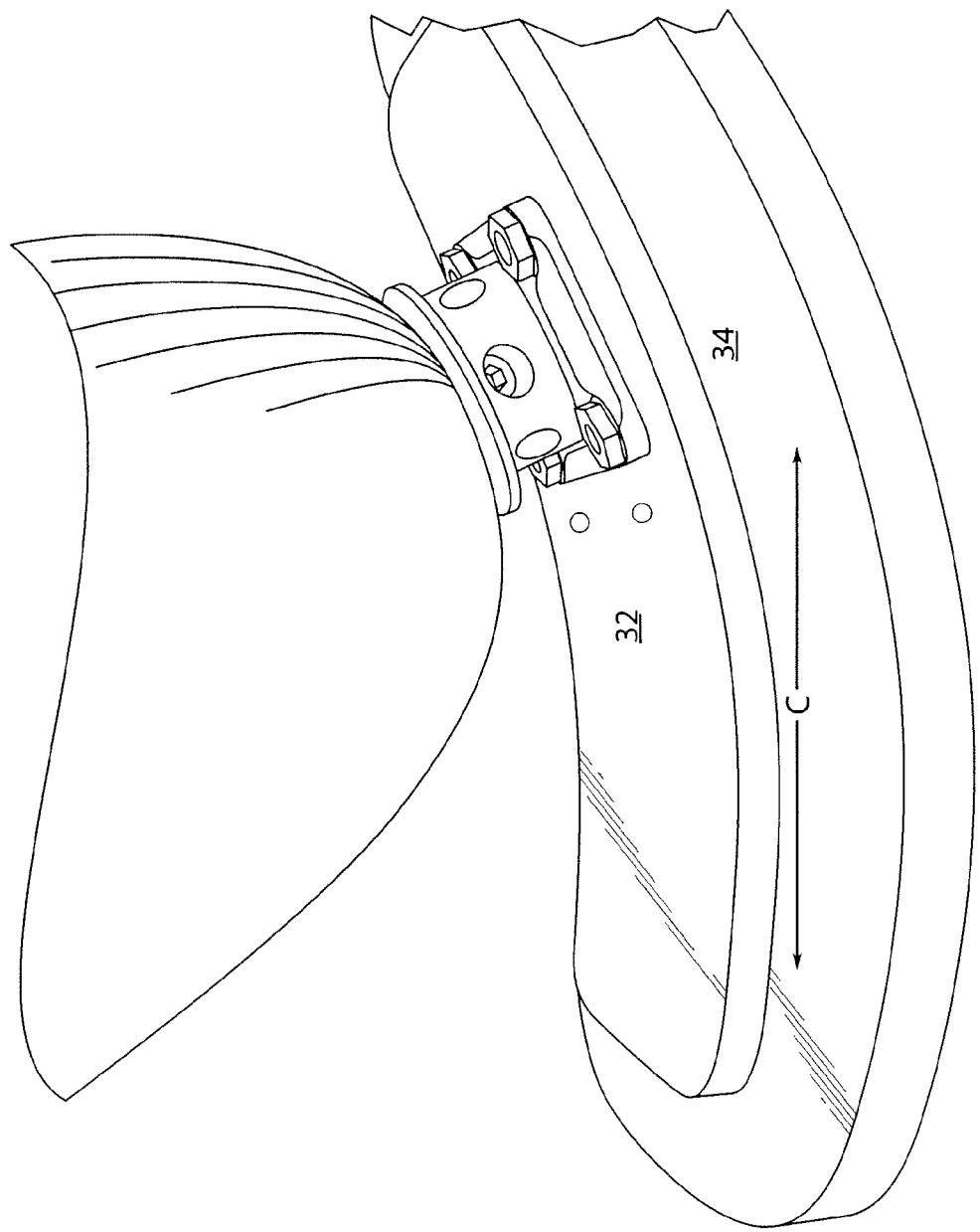
FIG. 4 is a side view of the prosthetic illustrating the bending motion.

FIG. 4 is a side view of the prosthetic illustrating the bending. The upper slide plate 32 resists this bending and reinforces the inherent stiffness of the lower base plate 34. However, the upper slide plate 32 is not attached to the lower base plate 34 other than the adapter 20 screws being journaled there through. Given the relatively low coefficient of friction interface between upper slide plate 32 and lower base plate 34, the upper slide plate 32 effectively slides along the lower base plate 34, leaving ample room for a differential flexing of the two plates 32, 34. This effectively forms a leaf spring suspension similar to those commonly used in wheeled vehicles. The leaf spring suspension adapts to the increasing weight, and then to decreasing weight as the foot 30 is planted and the stride shifts toward the toe (D). It also damps the foot strike and cushions the stride, resulting in a smoother progression from heel (A) to toe (D). Simultaneously, the curvilinear instep (B) promotes a rolling more natural stride replicating the effect of the arch of the human foot. Using two of the above-described prostheses, there is significantly improved ambulation, giving BAK amputees with a more comfortable and natural gait, at a suitable angle and orientation, with smooth and comfortable flex relative to the direction of travel.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims.

I claim:

1. A foreshortened prosthesis, comprising:
a socket for enveloping an amputee limb formed with an open end and a closed end;
an adapter attached distally to the closed end of said socket; and
a foot attached to said adapter, said foot further comprising, a lower base plate formed as a substantially flat peripherally-curvilinear member defining a rounded toe extending in advance of said adapter, a heel extending rearwardly of said adapter, and an inwardly recessed instep along one side of said lower base plate between said toe and heel, said lower base plate being fixedly attached to said adapter by a plurality of screws, and an upper slide plate sandwiched between said adapter and said lower base with said plurality of screws passing through, but said upper slide plate not being otherwise attached to said lower base, said upper slide plate having smaller length and width dimensions than said lower base plate and serving as a leaf spring suspension during a heel strike.

2. The foreshortened prosthesis according to claim 1, wherein said upper slide plate is generally rectangular.

3. The foreshortened prosthesis according to claim 1, wherein said lower base plate is at least 5% longer and wider than said upper slide plate.

4. The foreshortened prosthesis according to claim 1, wherein adapter is a non-articulating adapter.

5. The foreshortened prosthesis according to claim 1, further comprising a rubber pad attached beneath said lower base plate.

6. The foreshortened prosthesis according to claim 1, wherein said upper slide plate comprises a plastic member having a degree of lateral flexure.

7. The foreshortened prosthesis according to claim 6, wherein said lower base plate comprises a plastic member having a degree of lateral flexure.

8. The foreshortened prosthesis according to claim 7, wherein said upper slide plate contacts said lower base plate along a low coefficient of friction contact surface.

9. A prosthetic foot for use in a foreshortened prosthesis having a socket for enveloping an amputee limb formed with an open end and a closed end, and an adapter attached distally to the closed end of said socket, said prosthetic foot comprising: a bi-planar structure including a lower base plate fixedly attached to said adapter by a plurality of screws, and an upper slide plate sandwiched between said adapter and said lower base plate.

10. The prosthetic foot according to claim 9, wherein said plurality of screws pass through said upper slide plate, but said upper slide plate is not otherwise attached to said lower base plate.

11. The prosthetic foot according to claim 9, wherein said lower base plate is formed as a substantially flat peripherally-curvilinear member defining a rounded toe extending in advance of said adapter, a heel extending rearwardly of said adapter, and an inwardly recessed instep along one side of said lower base plate between said toe and heel.

12. The prosthetic foot according to claim 9, wherein said upper slide plate is of smaller length and width dimensions than said lower base plate and serves as a leaf spring suspension during a heel strike.

13. The prosthetic foot according to claim 12, wherein said upper slide plate is generally rectangular.

14. The prosthetic foot according to claim 13, wherein said lower base plate is at least 5% longer and wider than said upper slide plate.

15. The prosthetic foot according to claim 9, further comprising a rubber pad attached beneath said lower base plate.

16. The prosthetic foot according to claim 9, wherein said upper slide plate comprises a plastic member having a degree of lateral flexure.

17. The prosthetic foot according to claim 16, wherein said lower base plate comprises a plastic member having a degree of lateral flexure.

18. The prosthetic foot according to claim 17, wherein said upper slide plate contacts said lower base plate along a low coefficient of friction contact surface.

* * * * *